United States Patent [19]

Nakano et al.

[11] Patent Number: 5,070,161

[45] Date of Patent: Dec. 3, 1991

[54] HEAT-LATENT, CATIONIC POLYMERIZATION INITIATOR AND RESIN COMPOSITIONS CONTAINING SAME

[75] Inventors: Shinji Nakano, Takatsuki; Hiroharu Ohsugi, Hirakata; Yasuhiko Nakae, Sakai; Hisaki Tanabe, Yawata; Ryozo Takagawa, Toyonaka; Yoshio Eguchi, Ikeda; Koichi Tsutsui, Tanabecho; Takeshi Endo, Yokohama, all of Japan

[73] Assignee: Nippon Paint Co., Ltd., Osaka, Japan

[21] Appl. No.: 356,903

[22] Filed: May 25, 1989

[30] Foreign Application Priority Data

May 27, 1988 [JP] Japan .................................. 63-131170
May 27, 1988 [JP] Japan .................................. 63-131171
Dec. 28, 1988 [JP] Japan .................................. 63-333802
Mar. 3, 1989 [JP] Japan .................................. 1-526731
Mar. 29, 1989 [JP] Japan .................................. 1-794681
Apr. 25, 1989 [JP] Japan .................................. 1-106738

[51] Int. Cl.$^5$ .............................................. C08F 4/20

[52] U.S. Cl. ..................... 526/193; 524/379; 524/391; 526/204; 526/217; 526/320; 526/329.2; 526/329.7; 528/21; 528/89; 528/91; 528/92; 528/93; 528/233; 528/240; 528/241; 528/242; 528/408; 528/409; 528/423

[58] Field of Search ................ 524/379, 391; 526/320, 526/329.2, 329.7, 193, 204, 217; 528/93, 94, 21, 408, 423, 89, 91, 92, 239, 240, 241, 242, 285, 409

[56] References Cited

U.S. PATENT DOCUMENTS

| | | | |
|---|---|---|---|
| 3,542,828 | 11/1970 | Harris | 526/192 |
| 3,879,312 | 4/1975 | Udding et al. | 528/92 |
| 3,901,833 | 8/1975 | Flynn | 528/408 |
| 3,983,289 | 9/1976 | Nishizaki et al. | 528/89 |
| 4,069,055 | 1/1978 | Crivello | 528/92 |

Primary Examiner—Bernard Lipman
Attorney, Agent, or Firm—Millen, White & Zelano

[57] ABSTRACT

Benzyl pyridinium or ammonium salts of a non-nucleophilic anion are useful as a cationic polymerization initiator having a heat latency. A variety of resinous compositions containing this initiator is also disclosed.

3 Claims, No Drawings

HEAT-LATENT, CATIONIC POLYMERIZATION INITIATOR AND RESIN COMPOSITIONS CONTAINING SAME

BACKGROUND OF THE INVENTION

This invention relates to a novel class of cationic polymerization initiators having a heat-latency, i.e. which are normally inactive but are capable of initiating a cationic polymerization reaction only at an elevated temperature. The invention also relates to heat-curable resin compositions containing these initiators which are useful for the preparation of coating, adhesive, printing ink and other compositions.

A variety of cationic polymerization initiators are known including Friedel-Crafts catalysts such as aluminum chloride, boron trifluoride-ether complex, photo-degradable onium salts (S, Se, Te), diallyl iodonium salts and the like. These known initiators are generally not selective with respect to the reaction temperature. Therefore, an epoxy resin containing these initiators begins to cure even at room temperature.

Japanese Laid Open Patent Application (Kokai) Nos. 37003/83 and 37004/83 disclose another type of cationic polymerization initiators. They are aliphatic or aromatic sulfonium salts capable of generating carbonium cations upon heating to an elevated temperature. Initiators of this type are known as "heat-latent cationic polymerization initiator". Cation-polymerizable resins such as epoxy resins containing the heat-latent initiator are, therefore, normally inactive but capable of curing at a temperature above the cleaving temperature of the initiator. This provides a heat-curable, one-component epoxy resin composion having a greater storage-stability and a longer pot life.

The carbonium cations produced by the thermal cleavage of the heat-latent intiator may react with water or a hydroxy group-containing compound to generate protons which, in turn, catalyse various cross-linking reactions. Accordingly, the heat-latent cationic initiator may find uses in catalyzing the curing reaction of, for example, polyester and acrylic resins with melamine resins. This also provides systems having a greater storage stability.

The heat latent cationic initiator thus has a number of advantages over conventional cationic initiators or proton-donating catalysts. Unfortunately, the prior art sulfonium type initiators have a serious problem in that their sulfur-containing decomposition products are malodorous. This limits their uses in practice.

Accordingly, a strong need exists for a heat latent cationic polymerization initiator which obviates the above defects.

SUMMARY OF THE INVENTION

In one aspect, the present invention provides a compound of the formula:

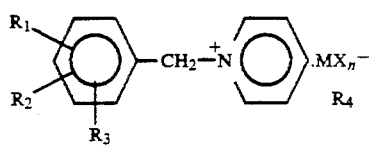

(I-a)

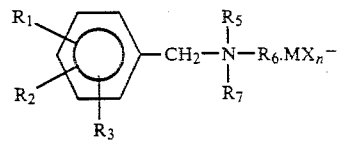

(I-b)

wherein $R_1$, $R_2$, $R_3$ and $R_4$ are each H, OH, halogen, an alkyl, an alkoxy, nitro, amino, an alkylamino, an alkanoyl cyano, an alkoxycarbonyl or carbamoyl; $R_5$, $R_6$ and $R_7$ are each an alkyl, an alkenyl or phenyl which may be substituted with nitro, cyano, amino, halogen, an alkyl or a dialkylamino, at least one of $R_5$, $R_6$ and $R_7$ being phenyl or the substituted phenyl; M is As, Sb, B or P; X is halogen; and n equals to the valency of the element M plus one.

In another aspect, the present invention provides a heat-curable resin composition comprising an amount of the above benzylpyridinium or benzylammonium compound effective to initiate the curing reaction of the composition at an elevated temperature.

The above benzylpyridinium or benzylammonium compound may be utilized in any one of the following systems:

I. Systems solely containing a cation-polymerizable monomer, polymer or a mixture thereof as a heat-curable component;
II. Systems containing a cation-polymerizable monomer, polymer or a mixture thereof and a polyol;
III. Systems containing a film-forming, hydroxy group-containing resin and a melamine resin;
IV. Systems capable of curing through a self-condensation reaction of an alkoxysilyl group-containing resin; and
V. Systems capable of curing through a co-condensation reaction of an alkoxysilyl group-containing resin and a hydroxy group-containing resin.

DETAILED DISCUSSION

1. Heat-Latent Cationic Initiator

The benzylpyridinium compound of the formula I-a:

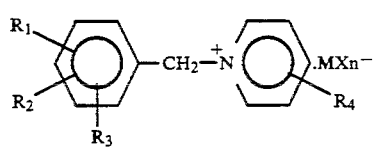

(I-a)

may be synthesized by reacting a corresponding benzyl halide of the formula II:

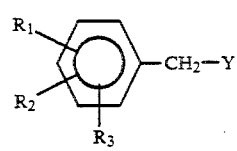

(II)

with a pyridine compound III-a of the formula:

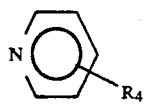

and then reacting the resulting benzylpyridium halide with an alkali metal salt of the complex anion $MXn^-$ to metathetically produce the compound I-a.

Similarly, the benzylammonium compound of the formula I-b:

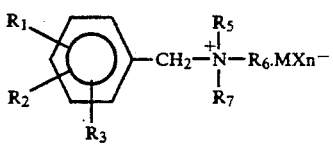

may be synthesized by reacting the benzyl halide (II) with a tertiary amine of the formula III-b:

and then reacting the resulting benzylammonium halide with an alkali metal salt of the complex anion $MXn^-$.

Among the compounds of formula I-a or I-b, those wherein at least one of $R_1$-$R_3$ is other than H are preferred. Also preferred are the compounds of the formula I-a wherein $R_4$ is cyano, a halogen or an alkanoyl at the 2 or 4-posion on the pyridine ring.

The compounds of the formula I-a or I-b are thermally cleaved at an elevated temperature to produce a benzyl cation of the formula:

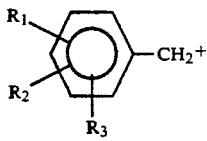

which, in turn, initiates a cationic polymerization chain reaction. However, these compounds are substantially inactive at a temperature below their cleaving points. Therefore, they find a number of valuable uses such as a hardener of one-component epoxy resins.

2. Heat-Curable Resin Compositions

I. Cation-polymerizable systems

Typical examples of cation-polymerizable monomers are those having a cation-polymerizable functional group such as epoxide, cyclic imine, cyclic ether cyclic ester, and other groups.

For use as a vehicle for coating compositions, adhesives, printing inks and the like, the resin composition may comprise a cation-polymerizable oligomer and/or polymer including the same structure as the above cation-polymerizable monomer in their molecules. The resin composition may be of the solventless type containing the above-mentioned cation-polymerizable monomer and/or a low molecular weight-polyol as a reactive diluent, or it may contain a conventional organic solvent for adjusting its viscosity to a suitable range for application.

Typical examples of cation-polymerizable resins are epoxy resins including bisphenol A—, bisphenol S— and bisphenol F epoxy resins; novolac type epoxy resins; diglycidyl ethers of glycols such as butanediol, hexanediol and hydrogenated bisphenol A; diglycidyl ethers of polyoxyalkylene glycols such as plyethylene glycol, polypropylene glycol and bisphenol A-alkylene oxide adducts; diglycidyl esters of dicarboxylic acids such as terephthalic acid, isophthalic acid, phthalic acid and adipic acid; and glycidyl ether-esters of hydroxycaboxylic acids such as p- and m-hydroxybenzoic acids.

Also included in examples of preferred cation-polymerizable resins are epoxide group-containing acrylic resins. These acrylic resins are produced by polymerizing a monomer mixture of glycidyl (meth)acrylate with a (meth)acrylic acid ester such as methyl (meth)acrylate, butyl (meth)acrylate, isobutyl (meth)acrylate and 2-hydroxyethyl (meth)acrylate optionally containing other comonomers such as styrene or its derivatives, acrylonitrile, vinyl acetate and the like.

Examples of usable polyols include low molecular weight-polyols such as ethylene glycol, propylene glycol, tetramethylene glycol, diethylene glycol, glycerine, trimethylolpropane and pentaerythritol. It should be noted that these low molecular weight-polyols produce H+ through a chain transfer reaction causing unwanted reactions of cation-polymerizable functional groups. This often results in a cured resin having a low average molecule weight and thus poor mechanical properties. Accordingly, it is more preferable to use an oligomer polyol such as polyether polyols, polycaprolactone polyol, polyester polyols and acryl polyols.

These polyols may be added to the resin composition in such an amount that their hydroxy function is 1 to 100 mole precent relative to the cation-polymerizable functional group. If the amount of polyol is too low, it is difficult to adjust the curing temperature of the resulting composition in a suitable range and the composition is not high solids. Conversely, excessive use of polyols adversely affects the curability of the entire composition.

The composition of this invention contains from 0.01 to 10%, preferably from 0.05 to 5% by weight of the resin solid content of the initiator compound of the formula I-a or I-b. If the amount of the initiator is deficient, the curability of the composition is not satisfactory. Conversely, excessive use of the initiator adversely affects the physical properties of cured composition, such as dark appearance and decreased water resistance.

The composition may contain conventional additives such as pigments, fillers and the like depending upon its intended use.

The resulting composition may be provided as the high solids or solventless type and has an increased storage stability at room temperature although curable at a temperature above the cleaving point of the initiator.

II. Systems containing melamine resins

Melamine resin-containing coating compositions or enamels are well-known in the art.

These compositions usually contain a proton-donor such as p-toluenesulfonic acid for catalyzing the crosslinking reaction with the melamine resin. Since the addition of a free acid to the composition tends to cause gelling of the entire composition upon storage, the catalyst is blocked partially or totally in its acid function with an amine which is volatile at the curing temperature of the composition. However, the curability of this type of composition is generally not compatible with the storage stability thereof.

The use of the cationic polymerization initiator of the present invention overcomes this problem. The initiator is substantially inactive until a critical temperature is reached. However, a carbonium cation is liberated from the initiator upon heating to a predetermined temperature and a proton is generated by the reaction of the carbonium cation with water or a hydroxy group-containing compound contained in the composition. This enables for the curability and storage stability of the composition to be compatible.

Various film-forming resins are used in the coating industry in combination with a melamine resin. Examples thereof include polyester resins, polylactone resins, epoxy resins, acrylic resins and the like.

Polyester resins are prepared by the condensation reaction of a polycarboxylic acid or its anhydride with a polyhydric alcohol. Any polyester resin having a hydroxy function at the terminal and/or middle of the polyester chain may be cross-linked with the melamine resin.

Hydroxy terminated polylactone resins may also be cross-linked with the melamine resin.

Epoxy resins having an epoxide function and a hydroxy function at the terminal and the middle of the molecule respectively such as bisphenol epoxy resins and novolac epoxy resins may be used in combination with the melamine resin.

Acrylic resins containing a plurality of hydroxy functions may be prepared by copolymerizing a hydroxy group-containing acrylic monomer such as 2-hydroxyethyl (meth)acrylate with one or more comonomers such as alkyl (meth)acrylates, e.g. methyl (meth)acrylate, butyl (meth)acrylate, isobutyl (meth)acrylate and 2-ethylhexyl (meth)acrylate; styrene or its derivatives; (meth)acrylonitrile; vinyl acetate and the like.

Melamine resins are prepared by reacting a triazine compound such as melamine, acetoquanamine or benzoguanamine with formaldehyde, and optionally etherifying the methylol function of the resulting condensate partially or totally with a lower alkanol such as methanol or butanol.

Thermosetting resin compositions comprising a hydroxy group-containing, film-forming resin and a melamine resin are well-known in the coating industry. Except for the use of the above-discussed cationic polymerization initiator, the composition of the present invention may be otherwise identical to these known compositions.

The weight ratio of the hydroxy group-containing, film-forming resin to the melamine resin ranges between 50:50 to 95:5 on the solid content basis.

The composition of this invention contains from 0.01 to 10%, preferably from 0.05 to 5% by weight of the resin solid content of the initiator of the formula I-a or I-b. If the amount of the initiator is deficient, the curability of the composition is not satisfactory. Conversely, excessive use of the intiator adversely affects the physical properties of cured composition such as dark appearance and decreased water resistance.

The composition may contain convenational additives such as pigments, fillers and the like depending upon its intended use.

III. Systems utilizing the self-condensation or co-condensation reaction of alkoxysilyl groups Japanese Patent Publication No. 33512/88 discloses a curable resin composition containing a vinyl polymer having a plurality of alkoxysilyl group-containing side chains, a polyhydroxy compound and a curing catalyst. It is believed that the composition cures through a self-condensation reaction between two alkoxysilyl groups:

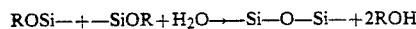

as well as a co-condensation reaction of an alkoxysilyl group and a hydroxy group:

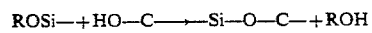

A variety of catalysts are disclosed as being capable of catalyzing the above reactions. These include amines such as butylamine, dibutylamine, t-butylamine, ethylenediamine and the like; organic metal compounds such as tetraisopropyl titanate, tetrabutyl titanate, tin octate, lead octate, zinc octate, calcium octate, dibutyltin diacetate, dibutyltin dioctate, dibutyltin dilaurate and the like; and acid catalysts such as p-toluenesulfonic acid, trichloroacetic acid and the like. The composition containing these catalysts is curable at room temperature. As is self-explanatory from this fact, the composition cannot be stored for a long period of time while containing the curing catalyst. When long term storage is desired, it is necessary to store the catalyst and the resin component separately and mix the two components immediately prior to use. This is inconvenient in practice and requires to use within a pot life. Other approach includes to reduce the amount of catalyst and blocking the amine or acid catalyst with a suitable acid or amine. Unfortunately they all have been proven unsatisfactory in terms of film properties, storage stabilities and the like.

Similar to the melamine resin-containing composition, the use of the cationic polymerization initiator of the present invention in the above-mentioned system overcomes these problems.

Examples of film-forming resins containing a plurality of alkoxysilyl groups include the following:

(1) Acrylic resins containing alkoxysilyl groups

A monomer having both an ethylenically unsaturated function and an alkoxysilyl function in the molecule forms a homopolymer or copolymer containing a plurality of alkoxysilyl groups by itself or with acrylic and/or other comonomers.

A first class of such monomers are alkoxysilylalkyl esters of acrylic or methacrylic acid of the formula:

wherein R is H or CH$_3$, R' and R" are each alkyl, x is an integer, and n is 0, 1 or 2.

Specific examples of these monomers include
γ-methacryloyloxypropyltrimethoxysilane,
γ-methacryloyloxypropylmethyldimethoxysilane,
γ-methacryloyloxypropyldimethylmethoxysilane, γ-methacryloyloxypropyltriethoxysilane,
γ-methacryloyloxypropylmethyldiethoxysilane,
γ-methacryloyloxypropyldimethylethoxysilane,
γ-methacryloyloxypropyltripropoxysilane,
γ-methacryloyloxypropylmethyldipropoxysilane,
γ-methacryloyloxypropyldimethylpropoxysilane,
γ-methacryloyloxypropyltributoxysilane,
γ-methacryloyloxypropylmethyldibutoxysilane, and
γ-methacryloyloxypropyldimethylbotoxysilane.

A second class of said monomers are adducts of (meth)acrylic acid with an epoxy group-containing alkoxysilane such as
β-glycidylpropyltrimethoxysilane or
β-(3,4-epoxycyclohexyl)ethyltrimethoxysilane.

Another class of alkoxysilyl group-containing monomers are adducts of a hydroxylalkyl (meth)acrylate such as hydroxyethyl (meth)acrylate, hydroxypropyl (meth)acrylate or 4-hydroxybutyl (meth)acrylate with an isocyanotoalkylalkoxysilane of the formula:

$$OCN(CH_2)_xSi(R')_n(QR'')_{3-n}$$

such as
γ-isocyanatopropyltrimethoxysilane,
γ-isocyanatopropylmethylmethoxysilane,
γ-isocyanatopropyltriethoxysilane or
γ-isocyanatopropylmethyldiethoxysilane.

A further class of alkoxysilyl group-containing monmers are adducts of glycidyl (meth)acrylate with an aminoalkylalkoxysilane such as
γ-aminopropyltrimethoxysilane,
γ-aminopropyltriethoxysilane,
3-(2-aminoethylamino)propylmethyldimethoxysilane,
3-(2-aminoethylamino)propyltrimethoxysilane,
γ-aminopropyldimethylmethoxysilane or
γ-aminopropylmethyldimethoxysilane.

Acrylic and/or other comonomers which may be copolymerized with the alkoxylsilyl group-containing monomer include alkyl (meth)acrylates, (meth)acrylic acid, (meth)acrylonitrile, (meth)arylamide, styrene, vinyl chloride, vinyl acetate and the like.

(2) Silicon-modified epoxy resins

The above-mentioned aminoalkylalkoxysilanes used for preparing an adduct with glycidyl (meth)acrylate may be reacted with an epoxy resin to produce a modified epoxy resin having a plurality of alkoxysilyl groups.

(3) Silicon-modified polyester resins

Polyester resins having a plurality of free carboxyl groups may be modified with the above-mentioned epoxy group-containing alkoxysilane to give silicon-modified polyester resins.

Polyesters having a plurality of hydroxy groups may be reacted with the above-mentioned isocyanatoalkylalkoxysilane to give silicone-modified polyester resins.

Typical examples of hydroxy group-containing resins include polyester resins, polylactone resins, epoxy resins and acrylic resins.

Polyester resins are prepared by the condensation reaction of a polycarboxylic acid or its anhydride with a polyhydric alcohol. Any polyester resin having a hydroxy function at the terminal and/or middle of the polyester chain may be employed.

Hydroxy terminated polylactone resins may also be employed.

Epoxy resins having an epoxide function and a hydroxy function at the terminal and the middle of the molecule respectively, such as bisphenol epoxy resins and novolac epoxy resins may be employed.

Acrylic resins containing a plurality of hydroxy functions may be prepared by copolymerizing a hydroxy group-containing acrylic monomer such as 2-hydroxyethyl (meth)acrylate with one or more comonomers such as alkyl (meth)acrylates, e.g. methyl (meth)acrylate, butyl (meth)acrylate, isobutyl (meth)acrylate and 2-ethylhexyl (meth)acrylate, styrene or its derivatives; (meth)acrylonitrile, vinyl acetate and the like.

Systems utilizing the self-condensation reaction of alkoxysilyl groups contain the above-mentioned silicon-containing resin and from 0.01 to 10%, preferably from 0.05 to 5% by weight of the resin solid content of the compound I-b.

Systems utilizing the co-condensation of alkoxysilyl group with hydroxy group contain the above-mentioned silicon-containing resin, an amount of hydroxy group-containing resin at a molar ratio of the hydroxy group per alkoxysilyl group of 0.01 to 10%, preferably from 0.05 to 5% by weight of the resin solid content of the compound I-a or I-b.

If the amount of compound I-a or I-b is deficient, the curability of the composition is not satisfactory. Conversely, excessive addition of the compound I-a or I-b adversely affects the physical properties of cured composition such as dark appearance and decreased water resistance.

The composition may contain conventional additives such as fillers, pigments and the like depending upon its intended use.

The resulting composition has an increased storage stability at room temperature but curable at a temperature above the cleaving point of the compound I-a or I-b. The curing time may vary with the curing temperature but usually within one hour.

The following examples are intended to further illustrate the present invention without limiting thereto. All parts and percents therein are by weight unless otherwise indicated.

EXAMPLES

Part I. Synthesis of Initiators

EXAMPLE I-1

1-(4-methoxybenzyl-2-chloropyridinium hexafluoroantimonate 4,698 g (0.03 mol) of 4-methoxybenzyl chloride and 10.22 g (0.09 mol) of 2-chloropyridine were reacted in 40 ml of methanol at 40° C. for 3 days. After the reaction, the solvent was evaporate in vacuo and ether-water was added to the residue to extract unreacted reactants in the etherial layer. To the aqueous layer containing the pyridinium chloride was added 7.764 g (0.03 mol) of sodium hexafluoroantimonate. The resulting crystals were suction filtered, washed and dried to give the title compound melting at 122°–124° C.

EXAMPLE I-2 to I-15

Analogous to Example I-1, various compounds of the formula I-a listed in the following table were synthesized.

Formula I-a:

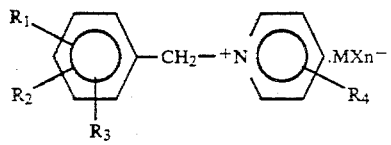

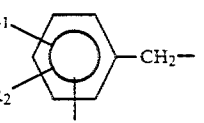

| Example No. | $R_3$ | $R_4$ | $MX_n^-$ |
|---|---|---|---|
| I-2 | 4-methylbenzyl | 2-Cl | $SbF_6^-$ |
| I-3 | 2,4-dimethylbenzyl | 2-acetyl | " |
| I-4 | benzyl | 2-Cl | $PF_6^-$ |
| I-5 | benzyl | " | $SbF_6^-$ |
| I-6 | 4-methoxybenzyl | 4-CN | " |
| I-7 | 4-methylbenzyl | " | " |
| I-8 | 4-t-butylbenzyl | " | " |
| I-9 | 4-nitrobenzyl | " | " |
| I-10 | 4-chlorobenzyl | " | " |
| I-11 | 2-methylbenzyl | 2-CN | " |
| I-12 | 2-chloro-5-fluoro-benzyl | " | " |
| I-13 | 2,3-dimethylbenzyl | " | " |
| I-14 | 4-methoxybenzyl | " | " |
| I-15 | 2,3-dimethylbenzyl | " | " |

EXAMPLE I-16

N-(p-methoxybenzyl)-N,N-dimethylanilinium hexafluoroantimonate 4,698 g (0.03 mol) of p-methoxybenzyl chloride and 3,638 g (0.03 mol) of N,N-dimethylaniline were reacted in 40 ml of methanol at 40° C. for 3 days. After the reaction, the solvent was evaporated in vacuo and ether/water was added to the residue to extract unreacted reactans in the etherial layer. To the aquous layer containing the ammonium chloride was added 7.77 g (0.03 mol) of sodium hexafluoroantimonate. The resulting crystals were suction filtered, washed and dried to give the titled compound.

NMR: 2.3 ppm (s, 3H, Me), 3.6 ppm (s, 6H, Me), 5.9 ppm (s, 2H, $CH_2$), 7.0 ppm (d, 2H, Ph), 7.3 ppm (d, 2H, Ph), 7.5-7.6 ppm (m, 5H, Ph).

EXAMPLES I-17-I-33

Analogous to Example I-16, various compounds of the formula I-b listed in the following table were sysntheized.

Formula I-b:

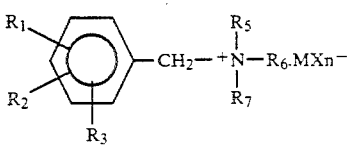

| Example No. | $R_3$ | $R_5$ $R_6$ $R_7$ | $MX_n^-$ |
|---|---|---|---|
| I-17 | p-methylbenzyl | N,N-dimethyl-anilinium | $SbF_6^-$ |
| I-18 | p-t-butylbenzyl | N,N-dimethyl-anilinium | " |
| I-19 | p-chlorobenzyl | N,N-dimethyl-anilinium | " |
| I-20 | p-nitrobenzyl | N,N-dimethyl-anilinium | " |
| I-21 | p-chlorobenzyl | N,N-dimethyl-anilinium | $PF_6^-$ |
| I-22 | p-methylbenzyl | N,N-dimethyl-anilinium | " |
| I-23 | " | N,N-dimethyl-N-(m-tolyl)ammonium | $BF_4^-$ |
| I-24 | benzyl | N,N-dimethyl-anilinium | $SbF_6^-$ |
| I-25 | benzyl | N,N-dimethyl-N-(p-tolyl)ammonium | " |
| I-26 | O-methylbenzyl | N,N-dimethyl-anilinium | " |
| I-27 | O-chlorobenzyl | N,N-dimethyl-anilinium | " |
| I-28 | 2,3-dimethylbenzyl | N,N-dimethyl-anilinium | " |
| I-29 | p-methoxybenzyl | N,N-dimethyl-anilinium | " |
| I-30 | p-methylbenzyl | N,N-dimethyl-N-(p-tolyl)ammonium | " |
| I-31 | " | N,N-dimethyl-N-(p-tolyl)ammonium | $PF_6^-$ |
| I-32 | 2-chloro-5-fluorobenzyl | N,N-dimethyl-anilinium | $SbF_6^-$ |
| I-33 | O-methylbenzyl | N,N-dimethyl-anilinium | $SbF_6^-$ |

Part II. Production of Vehicle Resins

Polyester Resin

A reaction vessel provided with a heater, stirrer, reflux condenser, water separator, fractional distillation column and thermometer was charged with 36 parts of hexahydrophthalic acid, 42 parts of trimethylolpropane, 50 parts of neopentyl glycol and 56 parts of 1,6-hexanediol. The mixture was heated to 210° C. with stirring. Then the mixture was heated to 230° C. at a constant rate over 2 hours while distilling out water formed as a by-product by the condensation reaction. The reaction was continued at 230° C. until an acid number of 1.0 was reached and stopped by cooling. After the addition of 153 parts of isophthalic acid, the reaction mixture was heated again to 190° C. and thereafter from 190° C. to 210° C. at a constant rate over 3 hours while distilling out formed water. When this temperature was reached, 3 parts of xylene was added and the reaction was continued until an acid number of 5.0 was reached. After cooling, the reaction mixture was diluted with 190 parts of xylene whereupon Polyester solution A was obtained.

Acrylic Resins

EXAMPLE II-2

Using a conventional technique, Acrylic resin solution A having a molecular weight of 3,500, a solution viscosity of M-N and a nonvolatile content of 60.5% was produced by solution polymerizing the following mixture at 120° C.

| Formulation | Parts |
|---|---|
| Methyl methacrylate | 28.11 |
| Styrene | 25.00 |
| Glycidyl methacrylate | 30.00 |
| n-Butyl acrylate | 2.59 |
| Isobutyl methacrylate | 1.88 |
| Azobisisobutyronitrile | 5.00 |

EXAMPLE II-3

Analogous to Example II-1, Acrylic resin solution B having a molecular weight of 4,200, a solution viscosity of U-V and a nonvolatile content of 60.2% was produced from the following mixture.

| Formulation | Parts |
|---|---|
| Methyl methacrylate | 23.11 |
| Styrene | 30.00 |
| Glycidyl methacrylate | 30.00 |
| n-Butylacrylate | 1.88 |
| Isobutyl methacrylate | 12.42 |
| Azobisisobutyronitrile | 5.00 |

EXAMPLE II-4

Analogous to Example II-1, the following mixture was solution polymerized at 120° C.

| Formulation | Parts |
|---|---|
| Methyl methacrylate | 23.1 |
| Styrene | 30.00 |
| n-Butyl acrylate | 2.59 |
| Isobutyl methacrylate | 1.88 |
| 2-Hydroxyethyl methacrylate | 12.42 |
| Azobisisobutyronitrile | 5.00 |

After the polymerization, 10.2 parts of p-vinylbenzoic acid was added to 60 parts (as solid content) of the resulting polymer and the mixture reacted at 200° C. until an acid number of 0.9 was reached. Acrylic resin solution C having a molecular weight of 4,300, a solution viscosity of Q-R and a nonvolatile content of 64.7% was obtained.

EXAMPLE II-5

A reaction vessel provided with a stirrer, thermometer, reflux condenser, nitrogen gas-introducing tube and dripping funnel was charged with 90 parts of SOLVESSO 100 and heated to 160° C. while introducing nitrogen gas. To the vessel was added dropwise the following monomer mixture at a constant rate:

| | |
|---|---|
| 2-Hydroxyethyl methacrylate | 23.20 parts |
| Methyl methacrylate | 38.85 parts |
| n-Butyl acrylate | 35.65 parts |
| Methacrylic acid | 2.30 parts |
| t-Butylperoxy-2-ethylhexanoate | 10.00 parts |

One hour after the addition, a mixture of 10 parts of xylene and 1 part of t-butylperoxy-2-ethylhexanoate was added dropwise at a constant rate over 30 minutes. The reaction was allowed to proceed to completion for 2 hours and stopped by cooling to give Acrylic Resin D.

EXAMPLE II-6

Analogous to Example II-5, Acrylic Resin E was prepared from the following monomer mixture:

| | |
|---|---|
| Isobutyl methacrylate | 1.88 parts |
| n-Butyl acrylate | 2.59 parts |
| Methyl methacrylate | 28.11 parts |
| Styrene | 25.00 parts |
| Glycidyl methacrylate | 30.00 parts |
| t-Butylperoxy-2-ethylhexanoate | 5.00 parts |

EXAMPLE II-7

Analogous to Example II-5, Acrylic Resin F was prepared from the following monomer mixture:

| | |
|---|---|
| 2-Hydroxyethyl methacrylate | 12.42 parts |
| n-Butyl acrylate | 2.59 parts |
| Methyl methacrylate | 23.11 parts |
| Styrene | 30.00 parts |
| Glycidyl methacrylate | 30.00 parts |
| t-Butylperoxy-2-ethylhexanoate | 5.00 parts |

Silicon Resins

EXAMPLE II-8

A reaction vessed used in Example II-5 was charged with 45 parts of xylene and heated to 130° C. while introducing nitrogen gas. To the vessel was added dropwise a mixture of 50 parts of γ-methacryloyloxypropyltrimethoxysilane and 4 parts of t-butylperoxy-2-ethylhexanoate at a constant rate over 3 hours.

30 minutes after the addition, the mixture was cooled to 90° C., and a mixture of 1 part of butylperoxy-2-ethylhexanoate and 5 parts of xylene was added thereto. The reaction was allowed to proceed to completion for additional 2 hours and stopped by cooling to give Silicon Resin A.

EXAMPLE II-9

Analogous to Example II-8, a mixture of 50 parts of γ-methacryloyloxypropylmethyldimethoxysilane and 4 parts of t-butylperoxy-2-ethylhexanoate was polymerized to give Silicon Resin B.

EXAMPLE II-10

Analogous to Example II-8, a mixture of 50 parts of γ-methacryloyloxypropyldimethylmethoxysilane and 4 parts of t-butylperoxy-2-ethylhexanoate was polymerized to give Silicon Resin C.

EXAMPLE II-11

Analogous to Example II-8, a mixture of 50 parts of γ-methacryloyloxypropyltriethoxysilane and 4 parts of t-butylperoxy-2-ethylhexanoate was polymerized to give Silicon Resin D.

EXAMPLE II-12

Analogous to Example II-8, a mixture of 25 parts of γ-methacryloyloxypropyltriethoxysilane, 25 parts of methyl methacrylate and 4 parts of t-butylperoxy-2-ethylhexanoate was polymerized to give Silicon Resin E.

EXAMPLE II-13

A reaction vessel provided with a stirrer, thermometer and reflux condenser was charged with 100 parts of Polyester Resin A obtained in Example I-1 and heated to 100° C. After the addition of 0.2 parts of dibutyltin dilaurate, 10 parts of KBK-9007 (chemically γ-isocyanatopropyltrimethoxysilane sold by Shin-Etsu Chemical Co., Ltd.) were added dropwise at a constant rate over 30 minutes and the reaction allowed to proceed to completion for additional 1 hour. After cooling, Silicon Resin F was obtained. The adsorption of NCO group at 1720 cm$^{-1}$ disappeared completely in the IR spectrometry of the resin.

EXAMPLE II-14

A reaction vessel provided with a stirrer, thermometer and reflux condenser was charged with 100 parts of bisphenol A diglycidyl ether and heated to 150° C. Then 100 parts of γ-aminopropyltrimethoxysilane were added dropwise at a constant rate over 1 hour and allowed to react for additional 1 hour. After cooling, Silicon Resin G was obtained.

Part III. Cation Polymerization Systems.

EXAMPLE III-1

0.5 parts of an initiator listed below was uniformly mixed with 100 parts of Acrylic Resin A, B or EPITOTO YD-014 (epoxy resin sold by Toto Kasei Co., Ltd.). The mixture was cast on a tinplate and baked at a temperature from 90° C. to 160° C. for 30 minutes. The curing state of each sample was observed and the results are shown in Table III-1.

Iniators

A: 1-(4-methoxybenzyl)-4-cyanopyridinium hexafluoroantimonate
B: 1-(4-methylbenzyl)-4-cyanopyridinium hexafluoroantimonate
C: 1-(4-t-butylbenzyl)-4-cyanopyridinium hexafluoroantimonate
D: 1-(4-nitrobenzyl)-4-cyanopyridinium hexafluoroantimonate
E: 1-(4-chlorobenzyl)-4-cyanopyridinium hexafluoroantimonate
F: 1-(2-methylbenzyl)-2-cyanopyridinium hexafluoroantimonate
G: 1-(2-chloro-5-fluorobenzyl)-2-cyanopyridinium hexafluoroantimonate
H: 1-(2,3-dimethylbenzyl)-2-cyanopyridinium hexafluoroantimonate
I: 1-(4-methoxybenzyl)-2-cyanopyridinium hexafluoroantimonate
J: 1-(2,3-dimethylbenzyl)-2-methylpyridinium hexafluoroantimonate
K: Boron trifluoride diethyl ether complex (for comparison)
L: 1-(p-t-butylbenzyl)tetrahydrothiophenium hexafluoroantimonate (for comparison)

TABLE III-1

| Run No. | Polymer | Initiator | 90 | 100 | 110 | 120 | 130 | 140 | 150 | 160 | Malodor |
|---|---|---|---|---|---|---|---|---|---|---|---|
| 1 | A | A | x | x | Δ | ○ | ○ | ○ | ○ | ○ | No |
| 2 | " | B | x | x | x | x | Δ | ○ | ○ | ○ | " |
| 3 | " | C | x | x | x | Δ | ○ | ○ | ○ | ○ | " |
| 4 | " | D | x | x | x | x | Δ | ○ | ○ | ○ | " |
| 5 | " | E | x | x | x | x | x | ○ | ○ | ○ | " |
| 6 | B | B | x | x | Δ | ○ | ○ | ○ | ○ | ○ | " |
| 7 | YD-014 | B | x | x | x | Δ | ○ | ○ | ○ | ○ | " |
| 8 | " | A | x | Δ | Δ | Δ | ○ | ○ | ○ | ○ | " |
| 9 | " | E | x | x | x | Δ | Δ | ○ | ○ | ○ | " |
| 10 | " | C | x | x | Δ | ○ | ○ | ○ | ○ | ○ | " |
| 11 | A | K | Gelling at R.T. immediately after mixing. | | | | | | | | " |
| 12 | A | L | x | x | x | x | Δ | ○ | ○ | ○ | Yes |

○: Fully cured;
Δ: Partially cured;
x: Tacky

EXAMPLE III-2

0.5 parts of the initiator was uniformly mixted with Acrylic Resin C. The mixture was cast on a tinplate and baked at a temperature from 90° C. to 160° C. for 30 minutes. The curing state of each sample was observed and results are shown in Table III-2.

TABLE III-2

| Run No. | Polymer | Initiator | 90 | 100 | 110 | 120 | 130 | 140 | 150 | 160 | Malodor |
|---|---|---|---|---|---|---|---|---|---|---|---|
| 1 | C | A | x | x | x | x | Δ | ○ | ○ | ○ | No |
| 2 | " | B | x | x | x | x | x | x | Δ | ○ | " |
| 3 | " | C | x | x | x | x | x | Δ | ○ | ○ | " |
| 4 | " | D | x | x | x | x | x | Δ | ○ | ○ | " |
| 5 | " | F | x | x | x | Δ | ○ | ○ | ○ | ○ | " |
| 6 | " | G | x | x | x | x | x | x | Δ | ○ | " |
| 7 | " | K | Gelling at R.T. immediately after mixing. | | | | | | | | " |

TABLE III-2-continued

| Run No. | Polymer | Initiator | Curing State Temperature, °C. | | | | | | | | Malodor |
|---|---|---|---|---|---|---|---|---|---|---|---|
| | | | 90 | 100 | 110 | 120 | 130 | 140 | 150 | 160 | |
| 8 | " | L | x | x | x | x | x | x | Δ | ○ | Yes |

○: Fully cured;
Δ: Partially cured;
x: Tacky

EXAMPLE III-3

0.5 parts of the initiator was uniformly mixed with 100 parts of ERL-4206(alicyclic epoxy resin sold by UCC). The mixture was cast on a tinplate and baked at a temperature from 90° C. to 160° C. The cured state of each sample was observed and the results are shown in Table III-3.

TABLE III-3

| Run No. | Polymer | Initiator | Curing State Temperature, °C. | | | | | | | | Malodor |
|---|---|---|---|---|---|---|---|---|---|---|---|
| | | | 90 | 100 | 110 | 120 | 130 | 140 | 150 | 160 | |
| 1 | ERL-4206 | H | x | Δ | ○ | ○ | ○ | ○ | ○ | ○ | No |
| 2 | " | I | x | Δ | ○ | ○ | ○ | ○ | ○ | ○ | " |
| 3 | " | J | x | Δ | ○ | ○ | ○ | ○ | ○ | ○ | " |
| 4 | " | K | Gelling at R.T. immediately after mixing. | | | | | | | | " |
| 5 | " | L | x | x | x | ○ | ○ | ○ | ○ | ○ | Yes |

○: Fully cured;
Δ: Partially cured;
x: Tacky

EXAMPLE III-4

0.5 parts of N-(2,3-dimethylbenzyl)-N,N-dimethylanilinium hexafluoroantimonate was uniformly mixed with Acrylic Resin F and 10 parts of ERL-4206. The mixture was cast on a tinplate and baked at 120° C. The curability of the composition as well as its storage stability was tested and the results are shown in Table III-4.

EXAMPLES III-5 to III-15

Analogous to Example III-4, the following compositions were tested for the curability and storate stability. The results are also shown in Table III-4.

Initiator of the formula:

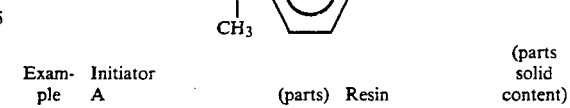

| Example | Initiator A | (parts) | Resin | (parts solid content) |
|---|---|---|---|---|
| III-5 | p-chlorobenzyl | 0.5 | Acrylic F | 70 |
| | | | ERL-4206 | 30 |
| III-6 | benzyl | 0.1 | Acrylic E | 90 |
| III-7 | p-chlorobenzyl | 2.0 | Acrylic E | 90 |
| III-8 | p-methylbenzyl | 0.07 | Acrylic E | 90 |
| III-9 | O-methylbenzyl | 0.5 | Acrylic E | 90 |
| III-10 | benzyl | 1.0 | Acrylic F | 90 |
| III-11 | p-chlorobenzyl | 0.05 | Acrylic F | 90 |
| III-12 | p-methylbenzyl | 4.0 | Acrylic F | 90 |
| III-13 | O-methylbenzyl | 0.3 | Acrylic F | 90 |
| III-14 | 2,3-dimethylbenzyl | 0.5 | ERL-4206 | 100 |
| III-15 | p-methylbenzyl | 0.06 | EPIKOTE1001 | 100 |

TABLE III-4

| | Example | | | | | | | | | | | |
|---|---|---|---|---|---|---|---|---|---|---|---|---|
| | III-4 | III-5 | III-6 | III-7 | III-8 | III-9 | III-10 | III-11 | III-12 | III-13 | III-14 | III-15 |
| Curability[1] | ⊙ | ○ | ○ | ○ | ○ | ○ | ⊙ | ⊙ | ⊙ | ⊙ | ⊙ | ○ |
| Storage Stability[2] | ○ | ⊙ | ⊙ | ⊙ | ○ | ⊙ | ○ | ⊙ | ⊙ | ○ | ○ | ⊙ |

[1]Appearance of cured film after the MEK rubbing test (100 reciprocations).
⊙: No change;
○: Slightly dissolved;
Δ: Whitening;
x: Dissolved
[2]Increase in viscosity after storing in a closed system at 40° C. for 2 weeks.
⊙: No increase;
○: Slightly increased;
Δ: Increased;
x: Gelling

Part IV. Cation Polymerizatioin System Containing Polyols

EXAMPLES IV-1

100 parts of Acrylic Resin A were thoroughly mixed with 0.5 parts of 1-(p-t-butylbenzyl)-4-cyanopyridinium hexafluoroantimonate and 2.95 parts of PLACCEL 308 (trifuctional polycaprolactone polyol having a molecular weight of 860 sold by Daicel Chemical Industries, Ltd.). The mixture was cast on a tinplate and baked at 130° C. or 150° C. for 30 minutes.

The curability determined by the finger test and the initial viscosity of the mixture are shown in Table IV-1.

EXAMPLES IV-2 to IV-8

Analogous to Example IV-1, the following compositions were tested for the curability and initial viscosity. The results are also shown in Table IV-1.

Initiator of the formula:

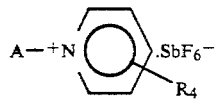

| Example | Initiator A | R4 | (parts) | Resin | (parts) |
|---|---|---|---|---|---|
| IV-2 | p-t-butylbenzyl, | 4-CN, | 0.5 | Acrylic A | 100 |
|   |   |   |   | Placcel 308 | 5.9 |
| IV-3 | p-t-butylbenzyl, | 4-CN, | 0.5 | Acrylic A | 100 |
|   |   |   |   | Placcel 308 | 11.8 |
| IV-4 | p-t-butylbenzyl, | 4-CN, | 0.5 | Acrylic A | 100 |
|   |   |   |   | Placcel 308 | 29.5 |
| IV-5 | 2,4-dichlorobenzyl, | 4-CN, | 0.5 | Acrylic A | 100 |
|   |   |   |   | Polyether-polyol 1) | 2.95 |
| IV-6 | 2,4-dichlorobenzyl, | 4-CN, | 0.5 | Acrylic A | 100 |
|   |   |   |   | Polyether-polyol | 5.9 |
| IV-7 | 2,4-dichlorobenzyl, | 4-CN, | 0.5 | Acrylic A | 100 |
|   |   |   |   | Polyether-polyol | 11.8 |
| IV-8 | 2,4-dichlorobenzyl, | 4-CN, | 0.5 | Acrylic A | 100 |
|   |   |   |   | Polyether-polyol | 29.5 |

1) Trifunctional polyetherpolyol, M.W. = 800

TABLE IV-1

| Temp. | IV-1 | IV-2 | IV-3 | IV-4 | IV-5 | IV-6 | IV-7 | IV-8 |
|---|---|---|---|---|---|---|---|---|
| 130° C. | Δ | Δ-○ | ○ | ○ | Δ | Δ-○ | ○ | ○ |
| 150° C. | Δ | ○ | ○ | ○ | Δ | ○ | ○ | ○ |
| Viscosity | L-M | J | G-H | F | K | I | G | D |

Curability:
○: Fully cured;
Δ: Fairly cured
x: Not cured
Viscosity: Measured by Gardener's bubble viscometer.

EXAMPLES IV-9 to IV-11

Analogous to Example IV-1, the following compositions were tested for the curability, storage stability and initial viscosity. The results are shown in Table IV-2.

TABLE IV-2

| | Example | | |
|---|---|---|---|
| | IV-9 | IV-10 | IV-11 |
| Initiator (1) (parts) | A 0.5 | B 0.5 | C 0.5 |
| Resin (parts) | Acrylic E 100 Placcel 308 2.95 | Acrylic E 100 1,6-hexane-diol | Acrylic E 100 Polyether-5 polyol (2) |
| Curability (3) | ⊚ | ⊚ | ○ |
| Storage stability (4) | ○ | ○ | ⊚ |
| Initial viscosity (5) | L-M | J | K |

(1) A = N-(p-t-butylbenzyl)-N,N-dimethylanilinium hexafluoroantimonate
B = (p-methylbenzyl)-N,N-dimethylanilinium hexafluoroantimonate
C = N-benzyl-N,N-dimethylanilinium hexafluoroantimonate
(2) Trifunctional polyetherpolyol, M.W. = 800
(3) Film appearance after the MEK rubbing test (100 reciprocations).
⊚: No change;
○: Slightly dissolved;
Δ: Whitening;
x: Dissolved
(4) Viscosity increase after storing in a closed system at 40° C. for 2 weeks.
⊚: No increase;
○: Slightly increased;
Δ: Increased;
x: Gelling
(5) Measured by Gardener's bubble viscometer.

Part V. Systems Containing Melamine Resin

EXAMPLE V-1

70 parts of PLACCEL 308, 30 parts of CYMEL 303 (melamine resin sold by Mitsui Toatsu Chemicals, Inc.) and 2 parts of 1-(4-methylbenzyl)-4-cyanopyridinium hexafluoroantimonate were thoroughly mixted. The mixture was cast on a tinplate and baked at 140° C. The curability and storage stability of the mixture are shown in Table V-1.

EXAMPLE V-2 to V-12

Analogous to Example V-1, the following compositions were tested for the curability and storate stability. The results are shown in Table V-1.

Initiater of the formula:

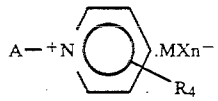

| Example | Initiator A, R4, MXn−, | parts | Resin, | parts |
|---|---|---|---|---|
| V-2 | 4-chlorobenzyl, 2-CH3, SbF6−, | 2 | Placcel 308 | 70 |
|   |   |   | Cymel 303 | 30 |
| V-3 | 2,4-dichlorobenzyl, 2-CH3, PF6−, | 2 | Placcel 308 | 50 |
|   |   |   | Cymel 303 | 50 |
| V-4 | 2-methylbenzyl, 2-CH3, PF6−, | 0.1 | Polyester A (solid content) | 90 |
|   |   |   | Cymel 303 | 10 |
| V-5 | 2,4-dimethylbenzyl, 2-Cl, PF4−, | 2 | Polyester A (solid content) | 60 |
|   |   |   | Yuban 20SE 1) (solid content) | 40 |
| V-6 | 4-methoxybenzyl, 3-Cl, BF4−, | 7 | Polyester A (solid content) | 70 |
|   |   |   | Yuban 20SE (solid content) | 30 |
| V-7 | benzyl, 2-CH3, SbF6− | 2 | Acrylic D (solid content) | 90 |
|   |   |   | Cymel 303 | 10 |
| V-8 | 2-chlorobenzyl, 2-CN, PF6−, | 2 | Acrylic D (solid content) | 60 |
|   |   |   | Yuban 20S (solid content) | 40 |
| V-9 | 4-methoxybenzyl, 4-Cl, SbF6−, | 0.5 | Acrylic D (solid content) | 70 |
|   |   |   | Yuban 20S (solid content) | 30 |
| V-10 | p-toluenesulfonic acid/ triethylamine salt (for comparison) | 2 | Placcel 308 | 70 |
|   |   |   | Cymel 303 | 30 |
| V-11 | p-dodecylbenzene-sulfonic acid/ pyridine salt (for comparison) | 2 | Plyester A (solid content) | 90 |
|   |   |   | Cynel 303 | 10 |

-continued $$A-\overset{+}{N}\underset{R_4}{\bigcirc}.MXn^-$$

| Example | Initiator A, R$_4$, MXn$^-$, | parts | Resin, | parts |
|---|---|---|---|---|
| V-12 | p-toluenesulfonic acid/pyridine salt (for comparison) | 2 | Acrylic D (solid content) | 60 |
| | | | Yuban 20S (solid content) | 40 |

1) Melamine resin sold by Mitsui Toatsu Chemicals, Inc.

TABLE V-1

| | Example | | | | | | | | | | | |
|---|---|---|---|---|---|---|---|---|---|---|---|---|
| | V-1 | V-2 | V-3 | V-4 | V-5 | V-6 | V-7 | V-8 | V-9 | V-10 | V-11 | V-12 |
| Curability[1] | ⊚ | ○ | ○ | ○ | ⊚ | ○ | ⊚ | ○ | ○ | ○ | ⊚ | ⊚ |
| Storage Stability[2] | ○ | ⊚ | ⊚ | ⊚ | ○ | ⊚ | ⊚ | ⊚ | ○ | Δ | x | x |

[1]Film appearance after the MEK rubbing test (100 reciprocations).
⊚: No change;
○: Slightly changed;
Δ: Whitening;
x: Dissolved
[2]Viscosity increase after storing in a closed system at 40° C. for 2 weeks.
⊚: No increase;
○: Slightly increased;
Δ: Increased;
x: Gelling

EXAMPLES V-13 to V-21

Analogous to Example V-1, the following compositions were tested for the curability and storage stability. The results are shown in Table V-2.

Initiator of the formula:

$$A-\overset{\underset{|}{CH_3}}{\underset{\underset{|}{CH_3}}{N^+}}-\bigcirc.MXn^-$$

| Example | Initiator A, MXn, parts | | Resin, parts | |
|---|---|---|---|---|
| V-13 | 4-methylbenzyl, SbF$_6^-$, | 2 | Placcel 308 | 70 |
| | | | Cymel 303 | 30 |
| V-14 | 4-chlorobenzyl, SbF$_6^-$, | 2 | Placcel 308 | 70 |
| | | | Cymel 303 | 30 |
| V-15 | 2,4-dichlorobenzyl, PF$_6^-$ | 1 | Placcel 308 | 50 |
| | | | Cymel 303 | 50 |
| V-16 | 2-methylbenzyl, PF$_6^-$ | 0.1 | Polyester A (solid content) | 90 |
| | | | Cymel 303 | 10 |
| V-17 | 2,4-dimethylbenzyl, BF$_4^-$ | 2 | Polyester A (solid content) | 60 |
| | | | Yuban 20S (solid content) | 40 |
| V-18 | 4-methoxybenzyl, BF$_4^-$, | 7 | Polyester A (solid content) | 70 |
| | | | Yuban 20S (solid content) | 30 |
| V-19 | benzyl, SbF$_6^-$, | 2 | Acrylic D (solid content) | 90 |
| | | | Cymel 303 | 10 |
| V-20 | 2-chlorobenzyl, PF$_6^-$, | 2 | Acrylic D (solid content) | 60 |
| | | | Yuban 20S (solid content) | 40 |
| V-21 | 4-methoxybenzyl, SbF$_6^-$, | 0.5 | Acrylic D (solid content) | 70 |
| | | | Yuban 20S (solid content) | 30 |

TABLE V-2

| | Example | | | | | | | | |
|---|---|---|---|---|---|---|---|---|---|
| | V-13 | V-14 | V-15 | V-16 | V-17 | V-18 | V-19 | V-20 | V-21 |
| Curability[1] | ⊚ | ○ | ○ | ○ | ⊚ | ○ | ⊚ | ○ | ○ |
| Storage Stability[2] | ○ | ⊚ | ⊚ | ⊚ | ○ | ⊚ | ⊚ | ⊚ | ○ |

[1]Film appearance after the MEK rubbing test (100 reciprocations).
⊚: No change;
○: Slightly changed;
Δ: Whitening;
x: Dissolved
[2]Viscosity increase after storing in a closed system at 40° C. for 2 weeks.
⊚: No change;
○: Slightly increased;
Δ: Increased;
x: Gelling

Part VI. Alkoxysilyl Group Self- or Co-condensation Systems

EXAMPLE VI-1

100 parts of Acrylic Resin D, 30.7 parts of Silicon Resin A, 5 parts of methanol and 2.62 parts of 1-benzyl-4-cyanopyridinium hexafluoroantimonate were thoroughly mixed. The mixture was cast on a steel plate, allowed to set for 2 hours and baked at 140° C. for 30 minutes. The curability and storage stability of the mixture are showen in Table VI-1.

EXAMPLES VI-2 to VI-14

Analogous to Example VI-1, the following compositions were tested for the curability and storage stability. The results are shown in Table VI-1.

Initiator of the formula:

$$A-N\underset{R_4}{\bigcirc}.MXn^-$$

| Example | Initiator A, R$_4$, MXn, parts | | Resin, parts | |
|---|---|---|---|---|
| VI-2 | 2-chlorobenzyl, 4-CN, SbF$_6^-$, | 2.58 | Acrylic D | 100 |
| | | | Silicon B | 28.5 |
| | | | Methanol | 5 |
| VI-3 | 2,4-dichlorobenzyl, 4-CN, SbF$_6^-$, | 2.54 | Acrylic D | 100 |
| | | | Silicon C | 26.9 |
| | | | Methanol | 5 |
| VI-4 | 2-methylbenzyl, 2-CN, SbF$_6^-$, | 2.72 | Acrylic D | 100 |
| | | | Silicon D | 36.2 |
| | | | Methanol | 5 |
| VI-5 | 4-nitrobenzyl, 2-CH$_3$, SbF$_6^-$, | 2.87 | Acrylic D | 100 |
| | | | Silicon E | 43.4 |
| | | | Methanol | 5 |

$$A-N\underset{R_4}{\overset{}{\bigcirc}}.MXn^-$$

| Example | Initiator A, R₄, MXn, parts | | Resin, parts | |
|---|---|---|---|---|
| VI-6 | 2-methylbenzyl, 4-F, PF₆⁻, | 2.87 | Polyester A<br>Silicon F<br>Methanol | 100<br>30<br>5 |
| VI-7 | 4-methoxybenzyl, H, PF₆⁻, | 2.87 | Polyester A<br>Silicon G<br>Methanol | 100<br>18<br>5 |
| VI-8 | 2-chlorobenzyl, 4-CN, SbF₆⁻, | 2 | Silicon A<br>Methanol | 100<br>5 |
| VI-9 | 2-chlorobenzyl, 4-CN, SbF₆⁻, | 2 | Silicon C<br>Methanol | 100<br>5 |
| VI-10 | 2-chlorobenzyl, 4-CN, SbF₆⁻, | 2 | Silicon F<br>Methanol | 100<br>5 |
| VI-11 | None (for comparison) | | Acrylic A<br>Silicon A<br>Methanol | 100<br>30.9<br>5 |
| VI-12 | dodecylbenzenesulfonic acid (for comparison) | 2.62 | Acrylic A<br>Silicon A<br>Methanol | 100<br>30.9<br>5 |
| VI-13 | None (for comparison) | | Silicon A<br>Methanol | 100<br>5 |
| VI-14 | dodecylbenzenesulfonic acid (for comparison) | 2 | Silicon A<br>Methanol | 100<br>5 |

TABLE VI-1

| | Example | | | | | | |
|---|---|---|---|---|---|---|---|
| | VI-1 | VI-2 | VI-3 | VI-4 | VI-5 | VI-6 | VI-7 |
| Curability¹ | ⊚ | ⊚ | ⊚ | ⊚ | ⊚ | ⊚ | ⊚ |
| Storage stability² | ○ | ○ | ○ | ○ | ○ | ○ | ○ |

| | Example | | | | | | |
|---|---|---|---|---|---|---|---|
| | VI-8 | VI-9 | VI-10 | VI-11 | VI-12 | VI-13 | VI-14 |
| Curability¹ | ⊚ | ⊚ | ⊚ | x | ⊚ | x | ⊚ |
| Storage stability² | ○ | ○ | ○ | ○ | x | ○ | x |

¹Film appearance after the MEK rubbing test (100 reciprocations).
⊚: No change;
○: Slightly changed;
Δ: Whitening;
x: Dissolved
²Viscosity increase after storing in a closed system at 40° C. for 2 weeks.
⊚: No change;
○: Slightly increased;
Δ: increased;
x: Gelling:

EXAMPLES VI-15 to VI-22

Analogous to Example VI-1, the following compositions were tested for the curability and storage stability. The results are shown in Table VI-2.
Initiator of the formula:

$$A-\underset{CH_3}{\overset{CH_3}{N}}-\bigcirc.MXn^-$$

| Example | Initiator A, MXn, parts | | Resin, parts | |
|---|---|---|---|---|
| VI-15 | benzyl, Sb₆⁻ | 2.62 | Acrylic A<br>Silicon A<br>Methanol | 100<br>30.7<br>5 |
| VI-16 | 2-chlorobenzyl, SbF₆⁻ | 2.58 | Acrylic A<br>Silicon B<br>Methanol | 100<br>28.9<br>5 |
| VI-17 | 2,4-dichlorobenzyl, SbF₆⁻ | 2.54 | Acrylic A<br>Silicon C | 100<br>26.9 |
| VI-18 | 2-methylbenzyl, SbF₆⁻ | 2.72 | Methanol<br>Acrylic A<br>Silicon D<br>Methanol | 5<br>100<br>36.2<br>5 |
| VI-19 | 4-nitrobenzyl, SbF₆⁻ | 2.87 | Acrylic A<br>Silicon E<br>Methanol | 100<br>43.4<br>5 |
| VI-20 | 2-methylbenzyl, PF₆⁻ | 2.87 | Acrylic A<br>Silicon F<br>Methanol | 100<br>30<br>5 |
| VI-21 | 4-methoxybenzyl, PF₆⁻ | 2.87 | Polyester A<br>Silicon G<br>Methanol | 100<br>18<br>5 |
| VI-22 | N-benzyl-N-(2-tolyl)-N,N-dimethylammonium hexafluoroantimonate | 2.58 | Silicon B<br>Methanol | 100<br>5 |

TABLE VI-2

| | Example | | | |
|---|---|---|---|---|
| | VI-15 | VI-16 | VI-17 | VI-18 |
| Curability¹⁾ | ⊚ | ⊚ | ⊚ | ⊚ |
| Storage stability²⁾ | ○ | ○ | ○ | ○ |

| | Example | | | |
|---|---|---|---|---|
| | VI-19 | VI-20 | VI-21 | VI-22 |
| Curability¹⁾ | ⊚ | ⊚ | ⊚ | ⊚ |
| Storage stability²⁾ | ○ | ○ | ○ | ○ |

¹⁾Film appearance after the MEK rubbing test (100 reciprocations).
⊚: No change; ○: Slightly changed;
Δ: Whitening; x: Dissolved
²⁾Viscosity increase after storing in a closed system at 40° C. for 2 weeks.
⊚: No change; ○: Slightly increased;
Δ: increased; x: Gelling;

What is claimed is:

1. In a heat curable resinous composition comprising a polymerization initiator and a resin capable of curing upon heating in the presence thereof, the improvement wherein the polymerization initiator is 0.01 to 10% by weight of the solid content of said resin of a compound of the formula:

$$\underset{R_2}{\overset{R_1}{\bigcirc}}-CH_2-\overset{+}{N}\underset{R_4}{\overset{}{\bigcirc}}.MXn^- \quad (I\text{-}a)$$

with $R_3$ on the first ring $$\underset{R_2}{\overset{R_1}{\bigcirc}}-CH_2-\underset{R_7}{\overset{R_5}{\underset{|}{N}}}-R_6.MXn^- \quad (I\text{-}b)$$

with $R_3$ on the ring wherein $R_1$, $R_2$, $R_3$ and $R_4$ are each H, OH, halogen, an alkyl, an alkoxy, nitro, amino, an alkylamino, an alkanoyl, cyano, an alkoxycarbonyl or carbamoyl;
$R_5$, $R_6$ and $R_7$ are each an alkyl, an alkenyl or phenyl which may be substituted with nitro, cyano, amino, halogen, an alkyl, an alkoxy or a dialkylamino, at least one of $R_5$, $R_6$ and $R_7$ being phenyl or the substituted phenyl;
M is As, Sb, B or P;
X is halogen; and
m equals the valency of the element M plus one.

2. The resinous composition according to claim 1, wherein said resin is a monomer or polymer having a cation polymerizable function, or a mixture thereof.

3. The resinous composition according to claim 2, wherein said cation polymerizable function is epoxide, cyclic imine, cyclic ether or vinyl.

* * * * *